United States Patent [19]

Heinz et al.

[11] Patent Number: 5,409,628
[45] Date of Patent: Apr. 25, 1995

[54] HAIR SHAMPOO

[75] Inventors: Dieter Heinz, Gustavsburg; Sabine Hinz, Pfungstadt, both of Germany

[73] Assignee: Goldwell, AG, Darmstadt, Germany

[21] Appl. No.: 116,269

[22] Filed: Sep. 3, 1993

Related U.S. Application Data

[63] Continuation of Ser. No. 918,699, Jul. 27, 1992, abandoned.

[30] Foreign Application Priority Data

Aug. 22, 1991 [DE] Germany .......................... 41 27 731.7

[51] Int. Cl.$^6$ .......................... C11D 3/02; C11D 3/37; C11D 1/835
[52] U.S. Cl. .......................... 252/174.17; 252/174.23; 252/547; 252/DIG. 14; 252/DIG. 13; 252/DIG. 6; 424/70.12; 424/70.13
[58] Field of Search ............. 252/174.17, 174.23, 252/547, DIG. 14, DIG. 13, DIG. 6; 424/70, 71

[56] References Cited

U.S. PATENT DOCUMENTS

| | | | |
|---|---|---|---|
| 3,964,500 | 6/1976 | Drakoff | 132/7 |
| 4,076,800 | 2/1978 | Marsh et al. | 424/70 |
| 4,087,518 | 2/1978 | Smith et al. | 424/70 |
| 4,364,837 | 12/1982 | Pader | 252/173 |
| 4,704,272 | 11/1987 | Oh | 424/70 |
| 4,839,168 | 6/1989 | Abe et al. | 424/74 |
| 4,885,107 | 12/1989 | Welzel | 152/106 |
| 5,035,832 | 7/1991 | Takamura | 252/174.15 |
| 5,152,914 | 10/1992 | Forske | 252/174 |

FOREIGN PATENT DOCUMENTS

| | | | |
|---|---|---|---|
| 0337354 | 10/1989 | European Pat. Off. | 252/174.17 |
| 0358216 | 3/1990 | European Pat. Off. | 252/174.17 |
| 2188060 | 9/1987 | United Kingdom . | |

OTHER PUBLICATIONS

Derwent WPI Acc. No. 92-171508/21, English Abstract of JP 4-108163 Apr. 1992.
Derwent Xram Acc. No. C70-R21464, English Abstract of JP 70007973, Mar., 1971.

Primary Examiner—Paul Lieberman
Assistant Examiner—Kery Fries
Attorney, Agent, or Firm—Birch, Stewart, Kolasch & Birch

[57] ABSTRACT

This invention refers to a hair shampoo composition presenting improved hair conditioning properties, comprising at least one anionic surfactant preferably mixed with a surface-active-alkyl polyglycoside in a proportion of 10:1 and 1:5, as well as an active hair conditioning composition comprising 0.1 to 1.0% by wt. of at least one cationic polymer, 0.1 to 1.0% by wt. of at least one water-soluble collagen or collagen derivative, and 0.5 to 8.0% by wt. of at least one polysiloxane, each calculated based on the total composition.

11 Claims, No Drawings

HAIR SHAMPOO

This application is a continuation of application Ser. No. 07/918,699, filed on Jul. 27, 1992, now abandoned.

BACKGROUND OF THE INVENTION

1. Field of the Invention

The present invention relates to a hair shampoo which not only provides thorough and gentle cleansing of the hair, but also shows an additional grooming and conditioning effect.

2. Description of the Related Art

Hair shampoos with conditioning properties are principally well-known. Thus, proposals have been made to add cationic polymers to shampoos based on traditional surfactants, e.g. quaternary cellulose derivatives, which deposit on the hair during the shampooing procedure and provide the hair with improved combability, soft touch and shine.

Furthermore, it has been suggested to add volatile and nonvolatile silicones to shampoos based on anionic surfactants. Although these shampoos do show a certain effect, they do not fulfill sufficiently all of requirements expected.

SUMMARY OF THE INVENTION

It has now been found, and this is the object of the present invention, that a hair shampoo on an aqueous basis provides both, adequate but gentle cleansing of the hair, and an excellent conditioning effect regarding touch, combability, volume and shine of the hair if it comprises at least one anion-active surfactant and, in addition, a mixture of hair conditioning ingredients which include 0.1 to 1.0% by weight of at least one cationic polymer and 0.1 to 1.0% by weight of at least one water-soluble collagen or collagen derivative, and 0.5 to 8.0% by weight of at least one polysiloxane, each calculated to based on the total composition of the hair shampoo.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Within the scope of the invention, preferred anionic surfactants are particularly the well-known $C_{10}$–$C_{18}$-alkyl ether sulfates, especially the $C_{12}$–$C_{14}$-alkyl ether sulfates or lauryl ether sulfates.

A preferred anionic surfactant comprises a mixture of $C_{12}$–$C_{14}$-alkyl ether sulfate with, e.g., 2 to about 10 ethylene oxide groups per molecule, and an α-olefin sulfonate, in particular a $C_{12}$–$C_{16}$-olefin sulfonate, preferably a $C_{14}$–$C_{16}$-olefin sulfonate, whereby the preferred weight proportion between the alkyl ether sulfate and the α-olefin sulfonate is within the range of about 5:1 to about 3:2.

Obviously, other well-known anionic surfactants may also be used, either on their own or in combination with one another, e.g. alkali salts of sulfosuccinic acid semi esters, particularly the disodium salt of monooctyl sulfosuccinate, and alkali salts of long-chain monoalkyl ethoxysulfosuccinates.

Other suitable anion-active surfactants are fatty alcohol sulfates, e.g. laurylsulfate, sarcosides, e.g. sodium lauryl sarcoside, monoglyceride sulfates, fatty acid amido sulfates prepared by ethoxylation and subsequent sulfation of fatty acid monoalkanolamides, taurides, alkylether carboxylic acids and finally alkali salts of long-chain alkyl phosphates which are also gentle, especially skin compatible detergents.

In combination with other anionic surfactants, well-known protein-fatty acid condensation products may also be used.

The proportion of the anion-active surfactants is normally between about 5 and about 30, preferably between about 8 and about 20% by weight of the total composition.

A survey of the anion-active surfactants used in shampoos may be found in the Monographie of K. Schrader, 2nd Edition (1989, Hüthig Buchverlag Heidelberg), pp.683 to 691.

In a preferred embodiment of the invention, the anion-active surfactant is used in a composition with at least one alkyl polyglycoside of the general formula $RO(R^1O)_tZ_x$, wherein Z is a reducing saccharide residue of 5 to 6 carbon atoms, R is an alkyl group of 8 to 18 carbon atoms, $R^1$ is an ethylene or propylene residue, t is a number from zero to 10, and x is a number from one to five, whereby the weight proportion of anionic surfactants to alkyl polyglycoside is between 10:1 and 1:5, in a ratio of from 10 to 30% by weight, calculated based on the total composition.

Mixtures of anion-active surfactants and alkyl polyglycosides and their use in hair shampoos are well-known per se, e.g. from EP-A 70,074.

The alkyl polyglycosides described therein are principally also suitable within the scope of the present invention; however, this invention preferably employs an alkyl polyglucoside having 9 to 11 carbon atoms within the alkyl chain and a condensation degree of less than 1.4, preferably about 1.35.

Naturally, the use of other alkyl polyglycosides is also within the scope of the invention, e.g. those having 12 to 18 carbon atoms within the alkyl chain and higher condensation degrees.

As mentioned above, the proportion of the mixture of anion-active surfactant(s) to alkyl polyglycoside(s) in the hair shampoo of this invention is between about 10 and about 30% by weight, based on the total composition of the shampoo. The preferred amount used is about 15 to 25% by weight.

The weight proportion of anionic surfactant(s) to alkyl polyglycoside(s) is between 10:1 and 1:5, preferably 5:1 and 1:1, particularly about 2 to 3:1.

Mixtures of sulfosuccinates and alkyl polyglycosides are already disclosed in EP-A 358 216; the mixtures described therein are especially suitable for use in the compositions according to this invention.

The shampoos of the invention obviously may contain further surface-active agents, especially non-ionic and amphoteric surfactants.

This composition also comprises, according to a further preferred embodiment of the invention, a surface-active amine oxide, preferably in a proportion of about 1 to about 3% by weight of the total composition. A preferred amine oxide is, e.g., lauryl dimethyl amine oxide, but other amine oxides may also be used within the scope of the invention.

The hair shampoos according of the invention may, as additional non-ionic surfactants, also include long-chain fatty acid mono- and dialkanolamides, for example coconut fatty acid monoethanolamide or myristic fatty acid diethanolamide. The proportion of these alkanolamides is preferably between about 0.2 and 2.5, especially between 0.5 and 2% by weight of the total composition.

Such compositions are e.g. the object of EP-A 70,076.

Further suitable non-ionic surfactants are the various sorbitan esters, e.g. polyethylenglycol sorbitan stearic acid ester, fatty acid polyglycol ester or fatty acid glyceride oxethylates, fatty alcohol polyglycol ethers and also co-condensates of ethylene oxide and propylene oxide, as they are available on the market under their trade name "Pluronics". These non-ionic surfactants are normally included in minor quantities, i.e. less than 2.5% by weight, calculated based on the total composition.

Finally the hair shampoos of the invention may also contain amphoteric surfactants if desired. These are especially the various well-known betaines such as fatty acid amido alkyl betaines, long-chain alkyl amino propionates as well as sulfobetaines. These substances and their use in hair shampoos are also well-known, e.g. from Schrader, cited above, which is hereby incorporated by reference.

The proportion of betaines in the compositions of the invention is regularly below 5% by weight, preferably below 3% by weight of the total composition.

The hair conditioning system of the invention comprises three different ingredients.

The first essential ingredient is a cationic polymer in a proportion of 0.1 to 1.0, preferably to 0.5 and particularly preferred of 0.15 to 0.4% by weight of the total composition.

EP-A 337 354 already discloses the use of cationic polymers per se in alkyl polysaccharide surfactants; however, it does not suggest the synergistic effect of these ingredients in the compositions according to the invention.

Suitable cationic polymers are, for example, cationic cellulose derivatives, as known under their trade name "Polymer JR", quaternized mono- and copolymers of diallyl dimethyl ammonium chloride, quaternary copolymers of vinyl pyrrolidone, e.g. with dimethyl aminoethyl methacrylate, polyamino polyamide, etc. As an example, reference is made to the list in the previously mentioned publication EP-A 337 354, at pp.3 to 7.

The second essential ingredient of the hair conditioning composition within the scope of the invention is a water-soluble collagen or a collagen derivative which is included in a proportion of 0.1 to 1.0, preferably 0.2 to 0.5, particularly 0.25 to 0.35% by weight, calculated based on the total composition.

Thereby, the weight ratio of the above defined cationic polymer to the collagen or collagen derivative is about 2:1 to 1:2, particularly about 1:1.

Suitable water-soluble collagens and collagen derivatives are particularly highly purified natural collagen substances extracted under mild conditions from animal skin, e.g. calf skin, having a triple helicoidal structure with telopeptides.

Also suitable is a so-called atelo collagen presenting again a triple helicoidal structure but where the telopeptides have been removed.

A particularly preferred collagen derivative is a desamido collagen which has been produced using an alkali treatment of animal skins, especially calf skins, showing a triple helicoidal structure but which has been partially desamidated.

The molecular weight of these collagens is normally in the range between about 250,000 and 300,000, typically between about 270,000 and 290,000.

Finally, the composition according to the invention also comprises 0.5 to about 8% by weight of a polysiloxane, particularly between 1 and 5, most preferred between 1.5 to 3% by weight.

As already mentioned, the use of polysiloxanes as conditioning agents in hair shampoos per se is principally known; but these substances, regardless whether low-volatile or less-volatile cyclic or linear polysiloxanes, on their own or in combination with each other do not lead to a satisfactory conditioning effect in shampoos.

Suitable polysiloxane compounds which yield, synergistic results in the claimed combinations of the invention are, e.g. dimethyl- or methylphenyl polysiloxanes, as they are known under their common names "dimethicone" or "phenyldimethicone" and also volatile silicone oils, e.g. substances known as hexymethyl disiloxanes or cyclomethicones. If necessary, also polyether-modified polysiloxanes may be used having partially surface-active properties, e.g. "Dimethicone copolyol" or "Cetyl-dimethicone copolyol".

The hair shampoo compositions according to the invention may obviously include all of the ingredients usually employed in these compositions.

As such are named:

Complexing agents, dyestuffs, preservatives, pH-regulants, viscosity regulants, e.g. inorganic salts such as sodium chloride or sodium sulfate, as far as they are not included in the basic surfactant mixtures anyway, fragrances, pearl gloss agents, thickeners, etc.

A list of these additive ingredients may be found in Schrader, cited above, at pp. 695-722, herein incorporated by reference.

The following examples, which are not to be construed as limiting the claims, illustrate the present invention.

EXAMPLE 1

| | |
|---|---|
| Sodium lauryl ether sulfate (1-4 EO units; 30%) | 20.00% by wt. |
| $C_9$-$C_{11}$-alkyl polyglycoside (x = 1.35), | 20.00 |
| $C_{14}$-$C_{16}$ α-olefin sulfonate, sodium salt (40%) | 10.00 |
| Lauryl dimethyl amine oxide (35%) | 4.50 |
| Coconut fatty acid protein condensate, sodium salt (30%) | 2.00 |
| Complexing agent (HEDP) | 0.50 |
| Opacifier | 2.00 |
| Solubilizer (polyoxyethylated hydrogenated castor oil fatty acid ester) | 1.00 |
| Cationic cellulose derivative (Polyquaternium-10) | 0.25 |
| Polydimethyl siloxane (Dimethicone) | 2.00 |
| Desamido collagen (Merck) | 0.25 |
| Perfume | 0.65 |
| Preservatives (parabens) | 0.25 |
| Water | @ 100.00 |

In a consumer test of two groups of 10 volunteers each, one group shampooed their hair with a shampoo of the composition of example 1 once daily, while the second group used a shampoo of the same composition but excluding desamido collagen.

After five days the hair of the volunteers were compared: It became evident that the hair of all volunteers who used the shampoo according to the invention showed distinctly improved shine, and the hair appeared more relaxed and smoother than the hair of the other volunteers who had applied the same shampoo but excluding desamido collagen.

EXAMPLE 2

| | |
|---|---|
| Lauryl ether sulfosuccinate, disodium salt (2–4 EO-units; 30%) | 20.00% by wt. |
| $C_{14}$–$C_{16}$ α-olefin sulfonate, sodium salt (40%) | 9.50 |
| $C_{12}$–$C_{14}$-alkyl glycoside (x = 1.8); 35% | 18.00 |
| Lauryl dimethyl amine oxide (35%) | 4.00 |
| Sorbitan polyoxyethylene 160-tristearate | 0.50 |
| $C_{12}$–$C_{14}$-fatty acid protein condensate (35%) | 1.50 |
| Complexing agent (EHDP) | 0.50 |
| Opacifier | 1.50 |
| Polydimethyl diallyl ammonium chloride (Polyquaternium-6) | 0.30 |
| Desamido collagen (Merck) | 0.25 |
| Dimethyl polysiloxane (dimethicone) | 2.30 |
| Preservatives (parabens) | 0.30 |
| Perfume | 0.70 |
| Phosphoric acid, 85% | 0.05 |
| Water | @ 100.00 |

This shampoo provides the hair with abundance and smoothness and a relaxed touch.

EXAMPLE 3

| | |
|---|---|
| Sodium lauryl ether sulfate (2 EO-units; 30%) | 18.00% by wt. |
| Lauryl ether sulfosuccinate, disodium salt (30%) | 12.00 |
| $C_9$–$C_{11}$-alkyl polyglycoside (x = 1.35); 35% | 15.00 |
| Lauryl dimethyl amine oxide (35%) | 6.00 |
| Sorbitan polyoxyethylene-160 tristearate | 0.50 |
| Coconut fatty acid protein condensate, sodium salt (30%) | 2.20 |
| Complexing agents (EDTA) | 0.30 |
| Opacifiers | 1.50 |
| Polyoxyethylated hydrogenated castor oil fatty acid ester | 1.00 |
| Quaternary copolymer of vinyl pyrrolidone/ dimethyl aminoethyl methacrylate (Polyquaternium-11) | 0.35 |
| Desamido collagen (Merck) | 0.20 |
| Cyclomethicone/dimethicone 1:1 (cyclic and linear dimethyl polysiloxane) | 2.50 |
| Perfume | 0.70 |
| Preservatives (parabens) | 0.30 |
| Water | @ 100.00 |

This shampoo presents the same favorable properties as those of Examples 1 and 2.

EXAMPLE 4

| | |
|---|---|
| Sodium lauryl ether sulfate, (2–4 EO units; 30%) | 27.5% by wt. |
| Coconut amidopropyl betaine (30%) | 5.0 |
| Abietic acid tetrapeptide condensate, (triethanolamine salt (30%) | 5.0 |
| Silicone oil | 2.0 |
| Cationic cellulose derivative (Polyquaternium-10) | 0.5 |
| Water-soluble collagen | 0.2 |
| Plant extracts | 0.2 |
| Pearl gloss concentrate (Euperlan$^R$ PK 900) | 7.5 |
| Parabens | 0.1 |
| Sodium chloride | 1.5 |
| Water | @ 100.00 |

EXAMPLE 5

| | |
|---|---|
| Monoethanolamine lauryl sulfate, 30% | 30.00% by wt. |
| Coconut alkyldimethyl ammonium betaine (Coco-Betaine); 30% | 10.0 |
| Coconut monoethanolamide, 35% | 3.0 |
| Silicone oil | 1.0 |
| Cationic cellulose derivative (Polyquaternium-10) | 0.3 |
| Water-soluble collagen | 0.3 |
| Parabens | 0.1 |
| Plant extracts | 1.0 |
| Water | @ 100.00 |

EXAMPLE 6

| | |
|---|---|
| Sodium lauryl ether sulfate (2–4 EO units; 30%) | 25.0% by wt. |
| Lauryl ether carboxylic acid, sodium salt (4–5 EO units; 90%) | 10.0 |
| Silicone oil | 1.5 |
| Desamido collagen (Merck) | 0.4 |
| Cationic cellulose derivative (Polyquaternium-10) | 0.5 |
| Herbal extracts | 0.3 |
| Parabens | 0.1 |
| Sulfur oil | 0.2 |
| Water | @ 100.0 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An aqueous based hair shampoo composition which comprises:
   a) about 5 to about 30% by weight of at least one anion-active surfactant, calculated on the basis of the total composition; and
   b) at least one hair conditioning substance comprising:
      i) 0.1 to 1.0% by weight of at least one cationic polymer, calculated on the basis of the total composition;
      ii) 0.1 to 1.0% by weight of at least one water-soluble collagen or collagen derivative, calculated on the basis of the total composition; and
      iii) 0.5 to 8.0% by weight of at least one polysiloxane, calculated on the basis of the total composition.

2. The hair shampoo according to claim 1, wherein said cationic polymer comprises 0.2 to 0.5% by wt. of a quaternary cellulose derivative, calculated on the basis of the total composition.

3. The hair shampoo according to claim 1, wherein said water-soluble collagen derivative comprises 0.2 to 0.5% by wt. of a desamido collagen, calculated on the basis of the total composition.

4. The hair shampoo according to claim 1, wherein said polysiloxane is present in an amount of 1 to 4% by weight, calculated on the basis of the total composition.

5. The hair shampoo according to claim 1, wherein the cationic polymer and the water-soluble collagen derivative are contained in a weight proportion of 1:2 to 2:1.

6. The hair shampoo according to any one of claims 2-5 and 1, wherein said said at least one anion-active surfactant is in admixture with at least one alkyl polyglycoside of the formula $$RO(R^1O)_tZ_x,$$

wherein Z is a reducing saccharide residue having 5 to 6 carbon atoms, R is an alkyl group of 8 to 18 carbon atoms, $R^1$ is an ethylene or propylene residue, t is a number from zero to ten and x is a number from one to five, in a proportion between 10 and 30% by weight, calculated on the basis of the total composition, whereby the weight proportion of anionic surfactants to alkyl polyglycoside is between 10:1 and 1:5.

7. The hair shampoo according to claim 1, wherein said anionic surfactant comprises a mixture of $C_{12}$-$C_{14}$-alkylether sulfate and an α-olefin sulfonate in a weight proportion of 5:1 to 3:2.

8. The hair shampoo according to claim 1, wherein said anionic surfactant comprises an alkali salt of a sulfosuccinic acid semi ester.

9. The hair shampoo according to claim 1, which further comprises 1 to 3% by weight of a surface-active amine oxide, calculated on the basis of the total composition.

10. The hair shampoo according to any one of claims 7 to 9 and 1, wherein said anionic surfactant is in admixture with an alkyl polyglycoside, which comprises a $C_9$-$C_{11}$-alkyl polyglycoside having a condensation degree (x) of less than 1.4.

11. The hair shampoo according to claim 6, wherein said alkyl polyglycoside comprises a $C_9$-$C_{11}$-alkyl polyglycoside having a condensation degree (x) of less than 1.4.

* * * * *